United States Patent [19]

Beaty, Jr.

[11] 4,051,017
[45] Sept. 27, 1977

[54] CATALYTIC HYDROCARBON REFORMING PROCESS AND CATALYST

[75] Inventor: William Ralph Beaty, Jr., Ponca City, Okla.

[73] Assignee: Continental Oil Company, Ponca City, Okla.

[21] Appl. No.: 662,184

[22] Filed: Feb. 27, 1976

Related U.S. Application Data

[62] Division of Ser. No. 540,915, Jan. 14, 1975, Pat. No. 3,966,588, which is a division of Ser. No. 360,274, May 14, 1973, Pat. No. 3,900,430.

[51] Int. Cl.² .................. C10G 35/06; C10G 35/08
[52] U.S. Cl. ................. 208/135; 208/136; 208/138; 252/463; 252/464; 252/466 PT
[58] Field of Search .............. 208/138, 216, 217; 252/463, 465, 466 J, 466 PT, 475

[56] References Cited

U.S. PATENT DOCUMENTS

| 2,890,162 | 6/1959 | Anderson et al. | 252/465 |
| 3,384,458 | 5/1968 | McCarthy et al. | 252/463 |
| 3,502,573 | 3/1970 | Pollitzer et al. | 208/139 |
| 3,852,190 | 12/1974 | Buss et al. | 208/138 |
| 3,900,430 | 8/1975 | Beaty | 208/138 |
| 3,966,588 | 6/1976 | Beaty | 208/216 |

*Primary Examiner* — Herbert Levine
*Attorney, Agent, or Firm* — Cortlan R. Schupbach, Jr.

[57] ABSTRACT

A process and catalyst for converting hydrocarbon oils to desirable components by contacting said oils in the presence of hydrogen under hydrocarbon conversion conditions with a catalyst comprising a catalytic amount of a catalytic metal supported on gamma alumina.

13 Claims, 4 Drawing Figures

FIGURE 1

DESULFURIZATION OF CLARIFIED OIL

FIGURE 2

DESULFURIZATION OF CLARIFIED OIL

FIGURE 3

DESULFURIZATION OF CLARIFIED OIL

FIGURE 4

CATALYTIC HYDROCARBON REFORMING PROCESS AND CATALYST

This application is a division of Ser. No. 540,915 filed Jan. 14, 1975, now U.S. Pat. No. 3,966,588 which is a division of Ser. No. 360,274 filed May 14, 1973, now U.S, Pat. No. 3,900,430.

BACKGROUND OF THE INVENTION

This invention relates to the conversion of hydrocarbon oils into desirable components. This invention further relates to the catalytic conversion of hydrocarbon oil into desirable components. This invention also relates to the catalytic conversion of hydrocarbon oil into desirable components by contacting said oil under hydrocarbon conversion conditions with a catalyst comprising a catalytic amount of a catalytic metal supported on gamma alumina.

PRIOR ART

Hydrocarbon oils as produced contain relatively low proportions of desirable components, such as gasoline, kerosene, jet fuels, n-paraffins, benzene, olefins, and the like, and, as a result, the history of the petroleum industry is a study in the continuing effort to convert crude hydrocarbon oils to more desirable components. Many processes, such as simple distillation, thermal cracking, catalytic cracking, reforming, hydrogenation, dehydrogenation, isomerization, desulfurization, hydrocracking, and the like are known for converting hydrocarbon oils into more desirable components. Many such processes require catalyts, and the effectiveness and the selectivity of such catalysts are prime importance in many processes. As a result, catalysts specifically tailored to produce particular results have been developed, and as a result of the well-known current shortage of crude oils, the search is continuing for improve catalysts having improved effectiveness and improved selectivity for converting hydrocarbon oils into desirable products.

It has long been known that alumina produced by the water hydrolysis of aluminum alkoxide possesses high activity as a catalyst, but such alumina has heretofore been too heavy (approximately 45 pounds per cubic feet) for extensive use as a catalyst.

Accordingly, a continuing search is in progress for improved catalysts which provide increased efficiencies and improved selectivity in hydrocarbon oil conversion reactions.

OBJECTS OF THE INVENTION

It is an object of the present invention to provide a process and catalyst for the conversion of hydrocarbon oils to desirable components. It is a further objective of the present invention to provide a process for the conversion of hydrocarbon oils to desirable components by contacting said hydrocarbon oils under hydrocarbon conversion conditions with a catalyst consisting essentially of an effective amount of a catalytic metal supported on gamma alumina. It is a further objective of the present invention to provide a process and a catalyst for reforming light hydrocarbon oils. It is a further objective of the present invention to provide a method and a catalyst for hydrodesulfurizing hydrocarbon oils. It is still a further objective to provide a method and a catalyst for dehyrogenating hydrocarbon oils. It is a further objective of the present invention to provide a method and a catalyst for isomerizing hydrocarbon oils to desirable components.

SUMMARY OF THE INVENTION

It has now been found that the objectives of the present invention are achieved in a process for converting hydrocarbon oils to desirable components by contacting said oils in the presence of hydrogen under hyrocarbon conversion conditions with a catalyst consisting essentially of a catalytic amount of at least one catalytic metal supported on gamma alumina produced by a process comprising:
  a. hydrolyzing aluminum alkoxides to produce an aqueous alumina slurry and an organic reaction product,
  b. contacting said aqueous alumina slurry with an effective amount of a suitable organic solvent to form a solvent-aqueous alumina mixture,
  c. evaporating the solvent and water, and
  d. forming said alumina into particles and calcining to produce gamma alumina.

DESCRIPTION OF PREFERRED EMBODIMENTS

Alumina produced by a process comprising:
  a. hydrolyzing aluminum alkoxides to produce an aqueous alumina slurry and an organic reaction product,
  b. contacting said aqueous alumina slurry with an effective amount of an organic solvent to form a solvent-aqueous alumina mixture,
  c. evaporating the solvent and water, and
  d. forming said alumina into particles and calcining to form gamma alumina has been found to be unexpectedly effective as a catalyst support. Aluminum alkoxides generally are suitable as a starting material although the tests described herein were conducted using aluminum alkoxides produced by the Zeigler process, wherein the alkoxide groups contain from about 2 to about 30 carbon atoms each.

A preferred method for the production of such alumina comprises:
  a. reacting aluminum alkoxides having alkoxy groups containing from about 1 to about 30 carbon atoms in the alkoxide portion with an aqueous alumina slurry and an organic portion;
  b. separating the organic portion and the aqueous alumina slurry;
  c. optionally further purifying the aqueous alumina slurry by solvent extraction, steam stripping and the like to further remove any remaining minor portions of the organic portion; and,
  d. contacting the aqueous alumina slurry with an effective amount of an organic solvent.

The aqueous alumina slurries suitable for use in the method of the present invention are those containing up to about 32 weight percent alumina as $Al_2O_3$ wherein said alumina has not previously been dried subsequent to its production from the raw materials used, ie, aluminum alkoxides, alum, alkali metal aluminates, and the like. Some dispersable aluminas were redispersed and treated according to the method of the present invention show improvements in desirable properties but are not substantially improved by comparison to comparable alumina which has not been previously dried. It has been found that aqueous alumina slurries can be concentrated by drying and the like to about 32 weight percent $Al_2O_3$ prior to treatment by the method to the present invention without substantial loss in the desirable parameters. Above about 32 weight percent $Al_2O_3$ losses in product quality were apparent. Preferred slurry compositions are from about 10 to about 20 weight percent $Al_2O_3$.

The aqueous alumina slurry so produced is contacted with an organic solvent to form a solvent-aqueous alumina mixture. Suitable solvents are selected from the group consisting of ethanol, propanol, isopropanol, butanol, hexanol, isobutanol, and tertiary butanol. Other solvents such as methanol and acetone have been found to be less effective, and, of the solvents listed above, ethanol and butanol are preferred because of their ready availability, in most processes wherein Zeigler alcohols are produced. The method of contacting the aqueous alumina slurry with the organic solvent is optional. Very desirable results have been achieved when at least enough solvent was added to form an azeotropic mixture of the solvent and the water present in the aqueous alumina portion so that the water may be removed by azeotropic evaporation during drying. Lesser or greater amounts of solvent may be used to achieve desirable improvements in alumina properties, but it has been observed that more desirable results are obtained when substantially an azeotropic amount is used. It has been found that very desirable results are obtained when up to about 20 percent by weight excess solvent is used.

For purposes of calculating the water present, the alumina is treated as $Al_2O_3$, thus the water of hydration is treated as removable water even though such water is not usually removed in the early drying operations; i.e., usually an alumina hydrate such as alpha alumina monohydrate is the product from the first drying step although such alumina may be further dried or calcined to unhydrated alumina such as gamma alumina and the like. In the drying step, it is necesary to have the azeotropic mixture described only in the mixture immediately prior to drying; i.e., prior washes or contacting may be conducted at any desired solvent to alumina slurry ratio. Azeotropic mixtures of the suitable solvents with water are listed in Lang's *Handbook of Chemistry*, 9th Edition, pages 1484–1485.

The drying may be conducted by any suitable method so long as the removal of an azeotropic vapor mixture is achieved. The alumina produced by such a process typically has an $Al_2O_3$ content from about 80 to about 100 weight percent, a pore volume from about 1.0 to about 2.75 cc/g, a surface area from about 225 to about 400 $M^2/g$, and a loose bulk density from about 7.5 to about 25 lb/ft$^3$. Such a method is set forth more fully in U.S. Ser. No. 246,028 entitled, "High-Porosity, High-Surface Area, Low-Bulk Density Alumina" filed Apr. 20, 1972, by William C. Ziegenhain now abandoned. Preferred alumina properties are a loose bulk density from about 9 to about 15 lb/ft$^3$, a cumulative pore volume from about 1.5 to about 2.50 cc/g, and a surface area from about 250 to about 350 m$^2$/g. A further desirable property is that a high proportion, typically more than 50 percent of the pore volume, consists of pores smaller than 1,000 in diameter with an average pore diameter from about 80 to about 150.

The alumina may be used in the powdered form although most catalytic applications require that the alumina be formed into particles and calcined to produce a finished catalyst. The alumina may be extruded by methods such as disclosed in U.S. Ser. No. 268,246 entitled, "Low-Density, High-Porosity Alumina Extrudates and a Method for Producting Said Extrudates," filed July 3, 1972, by Leach et al, now abandoned. Such extrudates typically have a loose bulk density from about 15 to about 35 lb/ft$^3$, a cumulative pore volume from about 0.8 to about 2.0 cc/g, and a surface area from about 150 to about 350 m$^2$/g. The catalytic elements may be incorporated into the catalyst by methods well known in the art such as impregnating, compositing, or otherwise formulating the finished catalyst material. Many such methods are well known to those skilled in the art and need not be discussed further.

The alumina described above is particularly desirable for use as a catalyst support or a catalyst component is any suitable reaction system and can be advantageously employed in hydrocarbon conversion reactions carried out at elevated temperatures in the presence of hydrogen such as, but not limited to, reforming, hydrocracking, hydrodesulfurization, isomerization, dehydrogenation, hydrogenation, and the like. The alumina may be impregnated with or otherwise composited with catalytically active materials such as metals or metallic compounds such as those selected from Groups IIIB, IVB, VB, VIB, VIIB, VIII, IB, IIB, as shown at pages 448–449 of the *Handbook of Chemistry and Physics*, Fortieth Edition, published by the Chemical Rubber Publishing Co., Cleveland, Ohio, indium, germanium, tin, and bismuth, hereinafter referred to as supported on the alumina. The amount of metals or metallic components composited with the alumina will, of course, depend upon the particular catalyst application and the particular metals used; for instance, with precious metals such as platinum, the amount of metal composited with the alumina will generally be within the approximate range of 0.01 to about 2 weight percent based on the weight of the catalyst. With metals of the iron group, larger amounts, typically 0.1 percent to about 20 percent by weight, of the metals based on the catalyst composition may be used. When two or more metals or metallic compounds are used, the total metal composited with the alumina will generally be within the approximate range of 1 percent to 30 percent by weight of the catalyst composition.

In the preparation of catalysts, the metals or metallic components may be added any convenient method. In particular, metals or metallic components may be introduced with the aluminum alkoxides, the hydrolysis water, or other streams to the hydrolysis zone so that the metallic component is present with the alumina as initially formed. The metals or metallic components may be added with the solvent to form the solvent-aqueous alumina slurry, added to the solvent-aqueous alumina slurry, blended with the alumina powder prior to extrusion, blended with the peptizing acids or water, added to the alumina prior to extrusion, and the like. The calcined extrudates may be dunked in solutions of catalytic metals or metallic compounds and dried, thereby impregnating the surface of such catalyst supports with catalytic materials. These and many other methods for incorporating the catalytic metals and metallic components into and onto the alumina catalyst supports are well-known to those skilled in the art and do not require further discussion. The choice of the particular method to be used in highly dependent upon the end objective of the catalyst manufacturer, and a discussion of the variables unique to each producer of catalysts is unnecessary and beyond the reasonable scope of the present application.

A catalyst for reforming light hydrocarbon stocks to produce gasoline, benzene, and the like is readily produced by incorporating with the alumina of the present application a catalytic amount of at least one metal selected from the group consisting of nickel, platinum, vanadium, rhenium, iridium, and the like. The metal is typically present in the catalyst in an amount equal to about 0.1 about 10 weight percent based on the catalyst weight. Such a catalyst is effective in reforming light hydrocarbon stocks under suitable hydrocarbon reforming conditions. Such conditions typically are a temperature from about 700 to about 1,000° F, a pressure from about 100 to about 1,000 psig, and a hydrogen to hydrocarbon ratio of about 1:1 'to about 20:1.

Metals or metallic compounds are used herein and hereinafter referred to as metals refers to metals as such and metallic compounds such as, but not limited to, metallic oxides; hydroxides; carbonates; halides; sulfates; phosphates; nitrates; citrates; oxalazes; metallic acids and salts such as molybdic acid, molybdate salts, platinic acid and salts thereof, halogenated platinum acids, and the like. A complete list of suitable metallic compounds is not considered necessary, since those listed above are illustrative metals and metallic compounds suitable for use in the production of catalysts as is well known to those skilled in the art.

Alumina produced by the method shown herein has been found to be unexpectedly effective in catalyst formulations wherein effective amounts of catalytic metals are supported on said alumina. No satisfactory explanation for the surprisingly increased catalyst activity when alumina so produced is used is now known.

Hydrocarbon oils are effectively hydrodesulfurized by contacting said hydrocarbon stocks under hydrodesulfurizing conditions of temperature, pressure, and hydrogen partial pressure with a catalyst consisting essentially of at least one metal selected from the group consisting of molybdenum, tungsten, chromium, nickel, cobalt, and the like supported on alumina as described above. Such catalysts may desirably consist of at least two metals in combination on the alumina support. Desirably the first component is selected from the group consisting of nickel and cobalt, and a second component is selected from the group consisting of molybdenum and tungsten. The metal is typically present in an amount equal to about 1.5 to about 25 weight percent based on the catalyst weight with said first component being present in an amount equal to from about 0.5 to about 5 weight percent and said second component being present in an amount equal to from about 1.0 to about 20 weight percent based on the catalyst weight. As in well known to those skilled in the art, such metals are typically deposited as salts, oxides, and the like. Typical hydrodesulfurizing conditions are a temperature from about 500° to about 850° F, a pressure from about 300 to about 5,000 psig, and a hydrogen to hydrocarbon molecular ratio from about 2:1 to about 100:1.

The catalysts of the present invention are effective in dehydrogenation of hydrocarbon oils, wherein the catalyst is formed by depositing with or upon the alumina a catalytic amount of at least one metal selected from the group consisting of chromium, platinum, palladium, nickel, molybdenum, and Group VIB and Group VIII metals. Such metals are typically present in an amount equal to from about 0.05 to about 5 weight percent of the catalyst. Typical reaction conditions for such dehydrogenation reactions are temperatures from about 600° to about 1,000° F, pressures from about 15 to about 500 psig.

Isomerization catalysts are prepared by depositing with or upon the alumina an effective amount of at least one metal selected from the group consisting of platinum, palladium, nickel, molybdenum, cobalt, copper, and the like. Such isomerization catalysts also optimally contain promoters such as halogens in an amount from about 2 to about 10 weight percent halogen based on the catalyst weight. The metals are typically present in an amount equal to about 0.01 to about 10 weight percent based on the catalyst. Isomerization reaction conditions vary widely dependent upon the particular reactions; however, typical conditions are a temperature from about 260° to about 950° F, a pressure from about 15 to about 1,000 psia, and a hydrocarbon to hydrogen ratio of about 0.2:1 to about 10:1.

The following examples will serve to further illustrate the catalysts and process of the present invention although it is noted that the invention is by no means restricted to the examples shown or the preceding description of preferred embodiments.

EXAMPLES

A solution was prepared by dissolving 48 g of molybdenum trioxide in 100 ml of 5 percent aqueous ammonia, and thereafter adjusting the resulting solution pH to about 5.0 with nitric acid. 64 g of water and 49 g of cobalt nitrate hexahydrate were then added to the mixture. The mixture was mixed with alumina extrudates having the properties shown below in Table 1, allowed to stand overnight, then dried at 250° F for about 2 hours and thereafter calcined at 900° F for 1 to 2 hours. Catalysts containing approximately the weight percentages molybdenum trioxide and weight percentages cobalt oxide shown below are produced. The catalyst properties are shown in Table 1.

|  | Catalyst A | Catalyst B | Catalyst C | Catalyst D |
|---|---|---|---|---|
| Alumina Type |  |  |  |  |
| Wt. % MoO | 15 | 15.4 | 15 | 12.5 |
| Wt. % CoO$^3$ | 3.5 | 3.81 | 3.5 | 3.5 |
| Surface Area, m$^2$/gm | 175 | 238 | 247 | 274 |
| Density, lbs/ft$^3$ | 45 | 27 | 27 | 42 |
| (gm/cc) | (0.72) | (0.43) | (0.43) | (0.67) |
| Nominal Pellet Diameter, Inches | 1/8 | 1/8 | 1/8 | 1/8 |
| Crush (5 mm Length - Dried at 120° C for 1 hr), lbs |  |  |  |  |
| High | 14 | 25 | 18 | 21 |
| Low | 6 | 7 | 3 | 3 |
| Average | 10 | 16 | 7 | 11 |

-continued

| Pore Volume, cc/gm | | Catalyst A | Catalyst B | Catalyst C | Catalyst D |
|---|---|---|---|---|---|
| 0- | 35 Ω Diameter | — | — | — | 0.03 |
| 0- | 40 | 0.01 | 0.01 | — | 0.05 |
| 0- | 50 | 0.02 | 0.03 | 0.01 | 0.08 |
| 0- | 65 | 0.02 | 0.08 | 0.03 | 0.25 |
| 0- | 80 | 0.10 | 0.22 | 0.12 | 0.42 |
| 0- | 100 | 0.18 | 0.34 | 0.32 | 0.50 |
| 0- | 120 | 0.24 | 0.43 | 0.46 | 0.51 |
| 0- | 150 | 0.39 | 0.51 | 0.55 | 0.53 |
| 0- | 200 | 0.43 | 0.56 | 0.60 | 0.54 |
| 0- | 250 | 0.43 | 0.60 | 0.63 | 0.56 |
| 0- | 350 | 0.44 | 0.64 | 0.65 | 0.57 |
| 0- | 500 | 0.44 | 0.66 | 0.68 | 0.58 |
| 0- | 800 | 0.44 | 0.69 | 0.71 | 0.61 |
| 0- | 1,000 | 0.45 | 0.71 | 0.74 | 0.62 |
| 0- | 2,000 | 0.45 | 0.77 | 0.83 | 0.63 |
| 0- | 5,000 | 0.50 | 0.91 | 0.93 | 0.64 |
| 0- | 10,000 | 0.50 | 0.92 | 0.94 | 0.65 |

The tests herein are comparative tests illustrating the effectiveness of the catalyst of the present invention by comparison to commercially available catalysts. For instance, Catalyst A was prepared using alumina produced by the water hydrolysis of aluminum alkoxides with no special treatment. As will be noted, the loose bulk density of this alumina is higher than that of Catalyst C, which is a catalyst prepared as described in the present application. Catalyst D is a commercially available catalyst having the properties shown. Catalyst B was produced from commercially available low-density alumina produced from alumina slurries produced by the sodium aluminate process.

Figure 1:
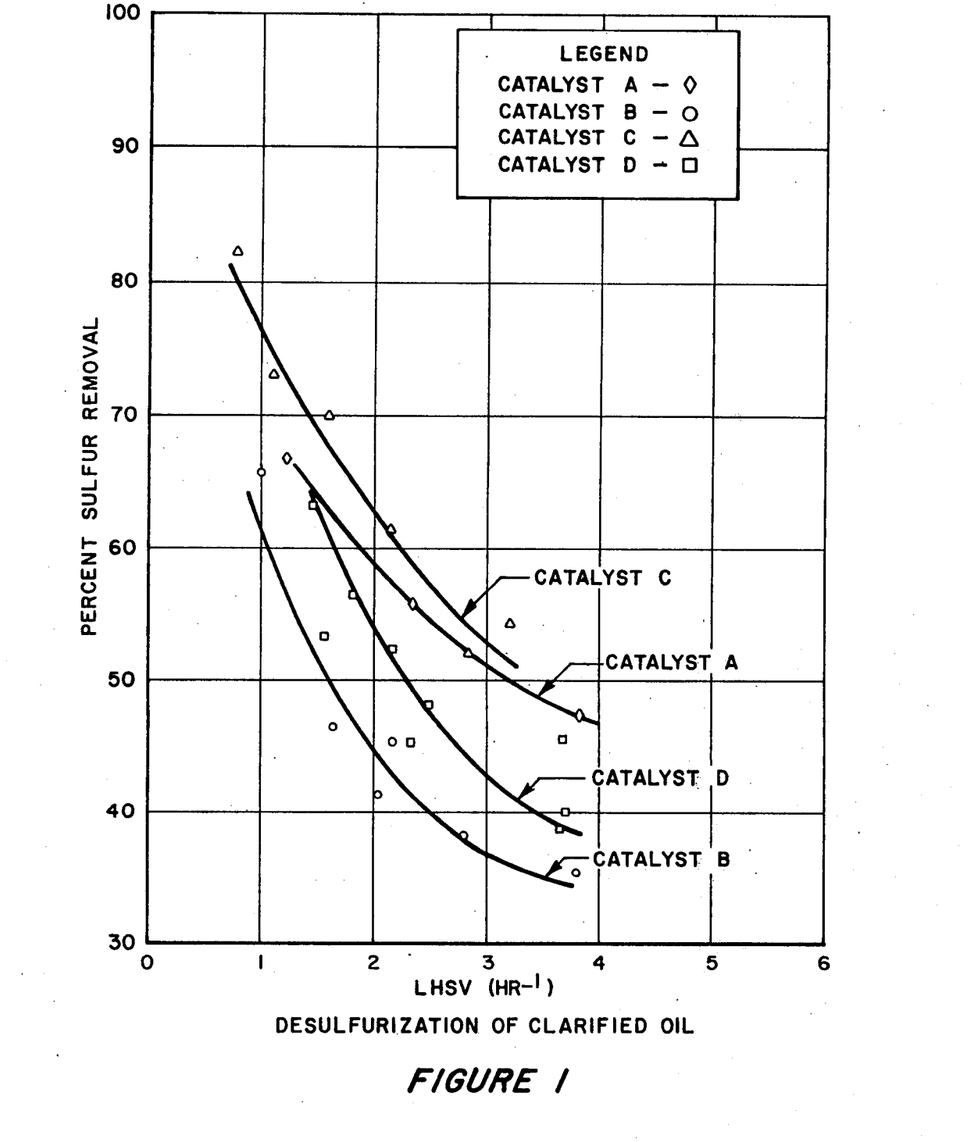
FIGS. 1, 2, 3, and 4 show graphically the data from comparative tests of catalysts prepared in accordance with the present invention with other catalysts.

The effectiveness of the catalyst of the present invention is shown by reference to FIGS. 1, 2, 3, and 4. In FIG. 1, it is noted that the catalyst of the present invention is substantially better than Catalysts A, B, or D. The oil used in the desulfurization tests had the properties shown below in Table II:

| API (60° F) | −3.2 |
|---|---|
| Total Sulfur, Wt. % | 3.50 |
| Total Sulfur, ppm | 35000 |
| Mercaptan Sulfur, ppm | 77 |
| Total Nitrogen, ppm | 1000 |
| Asphaltenes, Wt. % | 2.67 |
| Conradson Carbon, Wt. % | 5.10 |
| Ash, Wt. % | 0.13 |
| D-1160 Distillation | |
| IBP, ° F | 526 |
| 5% | 695 |
| 10 | 742 |
| 20 | 764 |
| 30 | 777 |
| 40 | 794 |
| 50 | 813 |
| 60 | 832 |
| 70 | 852 |
| 80 | 898 |
| 90 | 995 |
| 95 | — |
| EP | — |

The hydrotreating conditions were:

| HYDROTREATING CONDITIONS | |
|---|---|
| Temperature | 750° F |
| Pressure | 750 psig |
| H$_2$ Feed | 2000 SCFB |
| WHSV (Weight Hourly Space Velocity) | 2-10 hr$^{-1}$ |

Figure 2:
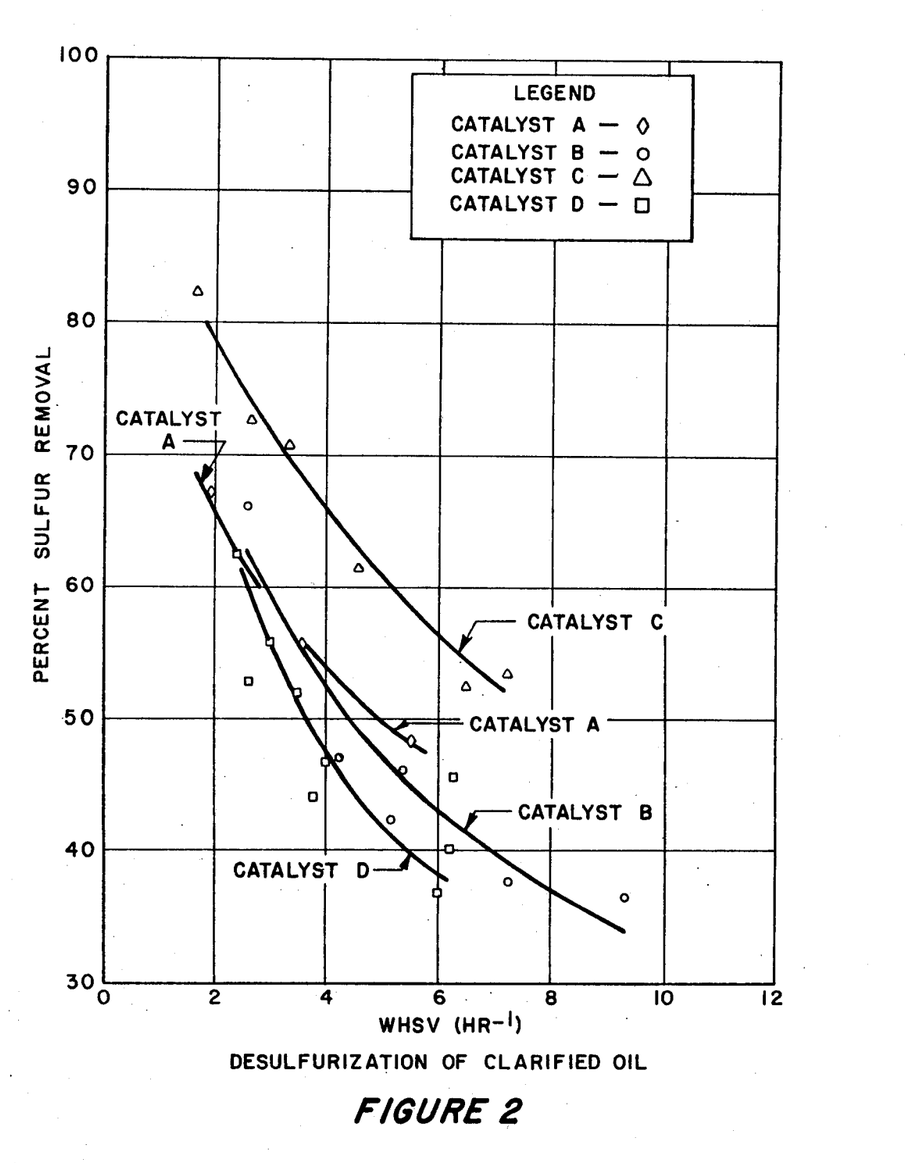

FIG. 2 is a different presentation of the data shown in FIG. 1. In particular, FIG. 2 shows the weight hourly space velocity, whereas FIG. 1 shows the liquid hourly space velocity. It will be noted that due to the light weight of the alumina support in the Catalyst C, the weight hourly space velocity data shows a surprising superiority as does FIG. 1 for the catalyst of the present invention.

It is noteworthy that improved results are achieved even though substantially less catalyst metal by weight is present in the given volume available for catalyst. This is particularly significant when it is considered that the metals are composited with the lighter alumina support in the same proportions by weight as with the heavier alumina supports. Accordingly, it is seen that a more efficient use of the catalytic metal components results, thus resulting in improved efficiency, lower operating costs, and the like.

Figure 3:
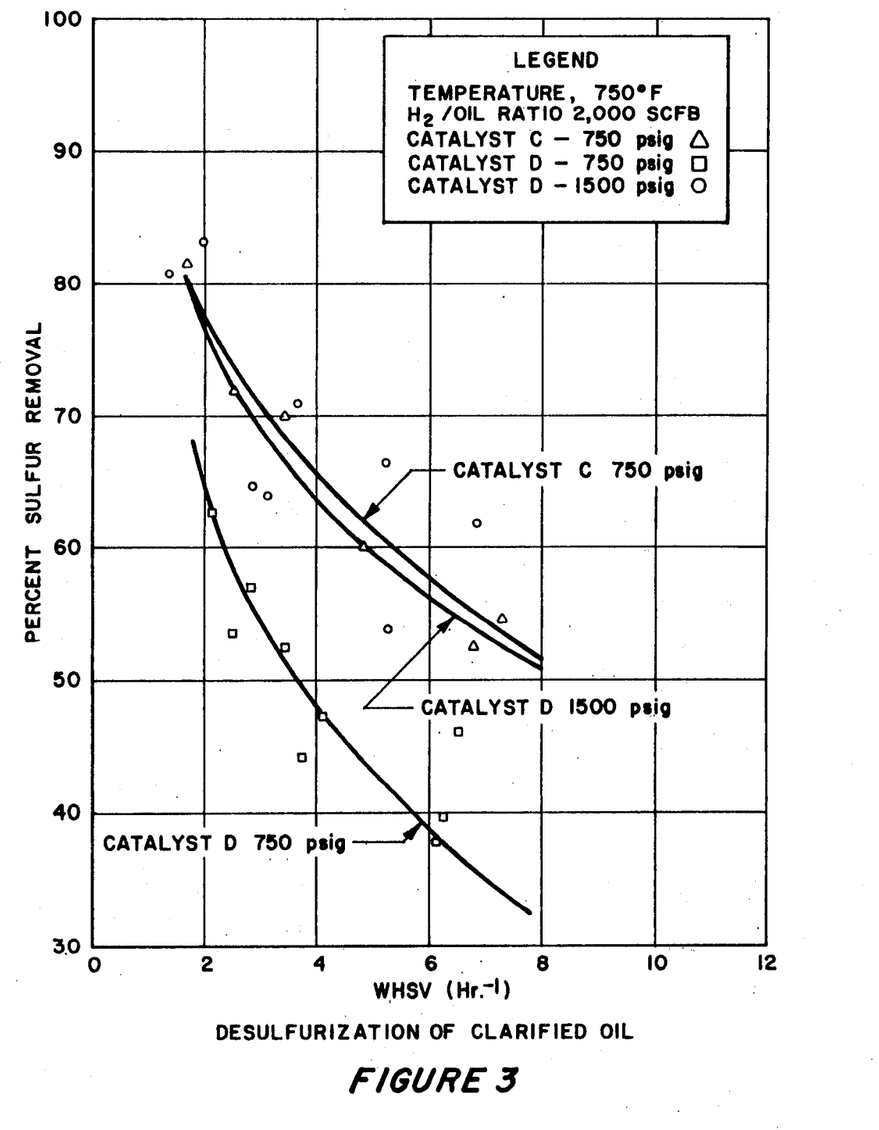
Figure 4:
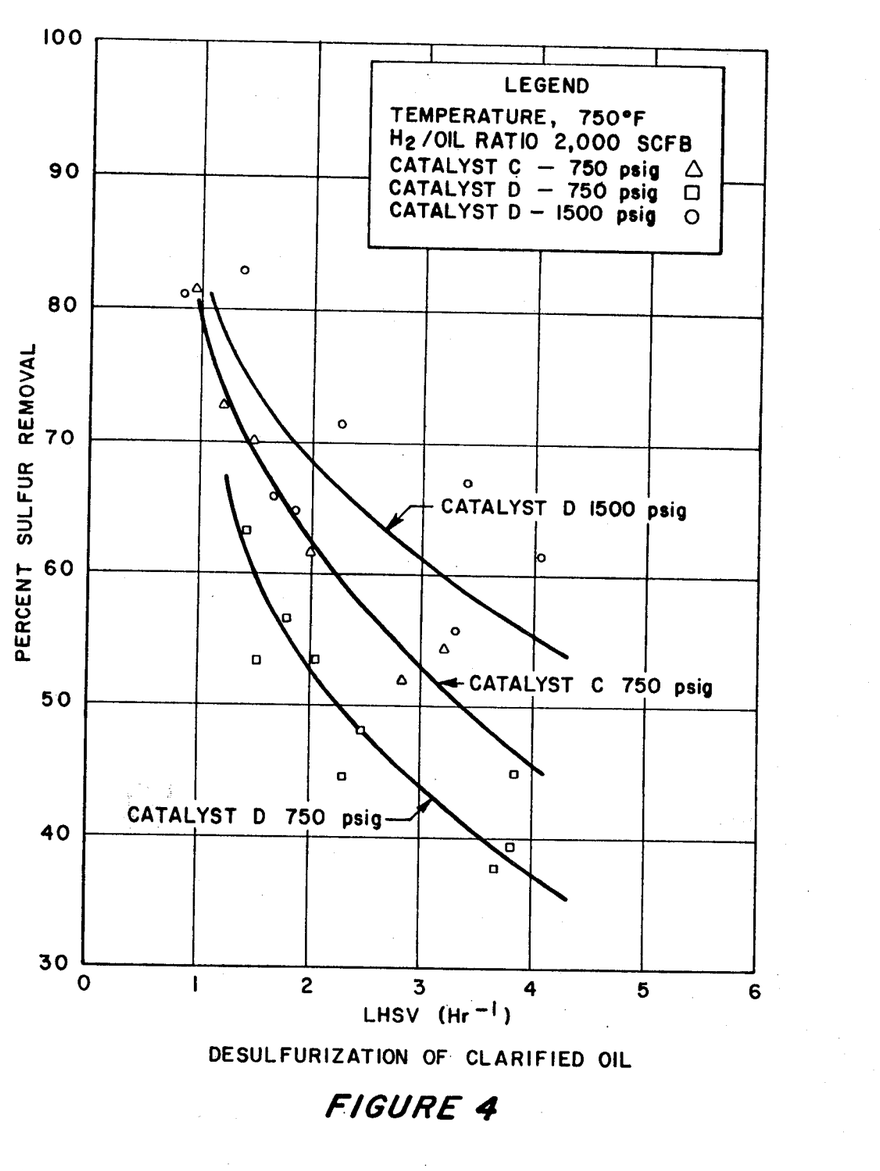

FIGS. 3 and 4 show comparisons of the effectiveness of the catalyst of the present invention with Catalyst D at varying pressures. It will be noted that the catalyst of the present invention is more effective at 750 psig than is Catalyst D at 1,500 psig in the WHSV comparison (FIG. III). It is obvious that a significant improvement in catalyst effectiveness has been achieved. FIG. 4 is a further comparison wherein Catalyst C is compared with Catalyst D at 750 psig. Again, it is clear that use of the catalyst of the present invention has achieved a surprising improvement in catalyst efficiency.

It has thus been demonstrated that catalysts produced with the alumina described in the present invention have surprisingly improved efficiency and a surprisingly high degree of activity.

Having thus described the invention, I claim:

1. A catalyst for hydrocarbon reforming consisting essentially of from about 0.01 to about 10 weight percent based on the catalyst weight of at least 1 catalytic metal selected from the group consisting of palladium, vanadium, platinum, rhenium and iridium, supported on a gamma alumina produced by a process consisting essentially of
   a. hydrolyzing aluminum alkoxides to produce an aqueous alumina portion containing up to about 32 weight percent Al$_2$O$_3$ and an organic reaction product;
   b. contacting said aqueous alumina slurry with an organic solvent selected from the group consisting of ethanol, propanol, isopropanol, butanol, hexanol, isobutanol and tertiary butanol in an amount sufficient to produce alumina having a cumulative pore volume (0–10,000A) from about 1.0 to about 2.75 cc/g, a surface area from about 225 to about 400 m$^2$/g and a loose bulk density from about 7.5 to about 25 lb/ft$^3$ upon drying to an Al$_2$O$_3$ content from about 80 to about 100 weight percent to form a solvent-aqueous alumina mixture;

c. drying said solvent-aqueous alumina mixture to produce alumina; and d. forming said alumina of (c) into particles and calcining to produce said gamma alumina.

2. The catalyst of claim 1 wherein said alumina particles of (d) have a loose bulk density from about 15 to about 35 lb/ft$^3$, a cumulative pore volume (0–10,000A) from about 0.8 to about 2.0 cc/g and a surface area from about 150 to about 350 m$^2$/g.

3. The catalyst of claim 1 wherein said alumina of (b) has a cumulative pore volume (0–10,000A) from about 1.5 to about 2.50 cc/g, a surface area from about 250 to about 350 m$^2$/g and a loose bulk density from about 9 to about 15 lb/ft$^3$.

4. The catalyst of claim 3 wherein more than 50 percent of the pore volume of (b) consists of pores smaller than 1000A in diameter.

5. The catalyst of claim 4 wherein the average pore diameter of the alumina (b) is from about 80 to about 150A.

6. A catalyst for hydrocarbon isomerization consisting essentially of from about 0.01 to about 10 weight percent on the catalyst weight of at least 1 catalytic metal selected from the group consisting of palladium, nickel, platinum, molybdenum, cobalt, and copper supported on gamma alumina produced by a process consisting essentially of a. hydrolyzing aluminum alkoxides to produce an aqueous alumina portion containing up to about 32 weight percent Al$_2$O$_3$ and an organic reaction product;

b. contacting said aqueous alumina slurry with an organic solvent selected from the group consisting of ethanol, propanol, isopropanol, butanol, hexanol, isobutanol and tertiary butanol in an amount sufficient to produce alumina having a cumulative pore volume (0–10,000A) from about 1.0 to about 2.75 cc/g, a surface area from about 225 to about 400 m$^2$/g and a loose bulk density from about 7.5 to about 25 lb/ft$^3$ upon drying to an Al$_2$O$_3$ content from about 80 to about 100 weight percent to form a solvent-aqueous alumina mixture;

c. drying said solvent-aqueous mixture to produce alumina, and;

d. forming said alumina of (c) into particles and calcining to produce said gamma alumina.

7. The catalyst of claim 6 wherein said alumina of (b) has a cumulative pore volume (0–10,000A) from about 1.5 to about 2.50 cc/g; a surface area from about 250 to about 350 m$^2$/g and a loose bulk density from about 9 to about 15 lb/ft$^3$.

8. The catalyst of claim 6 wherein more than 50 percent of the pore volume of (b) consists of pores smaller than 1000A in diameter.

9. The catalyst of claim 6 wherein the average pore diameter of the alumina (b) is from about 80 to about 150A.

10. A process for reforming light hydrocarbon stocks at a hydrogen to hydrocarbon ratio of about 1:1 to about 20:1 respectively, at temperatures of from about 700° to 1,000° F and pressures of from about 100–1,000 pounds per square inch gauge with a catalyst consisting essentially of from about 0.1 to about 10 weight percent based on the catalyst weight of at least 1 catalytic metal selected from the group consisting of palladium, vanadium, platinum, rhenium, and iridium supported on gamma alumina produced by a process consisting essentially of;

a. hydrolyzing aluminum alkoxides to produce an aqueous alumina slurry and an organic reaction product, b. contacting said aqueous alumina slurry with an organic solvent selected from the group consisting of ethanol, propanol, isopropanol, butanol, hexanol, isobutanol and tertiary butanol in an amount sufficient to produce alumina having a cumulative pore volume (0–10,000A) from about 1.0 to about 2.75 cc/g, a surface area from about 225 to about 400 m$^2$/g and a loose bulk density from about 7.5 to about 25 lb/ft$^3$ and a loose bulk density from about 7.5 to about 25 lb/ft$^3$ upon drying to an Al$_2$O$_3$ content from about 80 to about 100 weight percent to form a solvent-aqueous alumina mixture, c. drying said solvent-aqueous alumina mixture to produce alumina, and d. forming said alumina into particles and calcining to produce said gamma alumina.

11. The process of claim 10 wherein said particles of (d) have a loose bulk density from about 15 to about 35 lb/ft$^3$, a cumulative pore volume from about 0.8 to about 2.0 cc/g, and a surface area from about 150 to about 350 m$^2$/g.

12. A process for isomerization of hydrocarbon oil by contacting said oil with hydrogen at a hydrocarbon to hydrogen ratio of about 0.2:1 to about 10:1 respectively, under conditions of from about 260° to about 950° F and a pressure of about 15 to about 1,000 pounds per square inch actual with a catalyst consisting essentially of about 0.1 to about 10 percent by weight based on the weight of the catalyst of a metal selected from the group consisting of palladium, platinum, molybdenum, nickel, cobalt, and copper supported on a gamma alumina produced by a process consisting essentially of:

a. hydrolyzing aluminum alkoxides to produce an aqueous alumina slurry and an organic reaction product, b. contacting said aqueous alumina slurry with an organic solvent selected from the group consisting of ethanol, propanol, isopropanol, butanol, hexanol, isobutanol and tertiary butanol in an amount sufficient to produce alumina having a cumulative pore volume (0–10,000A) from about 1.0 to about 2.75 cc/g, a surface area from about 225 to about 400 m$^2$g and a loose bulk density from about 7.5 to about 25 lb/ft$^3$ upon drying to an Al$_2$O$_3$ content from about 80 to about 100 weight percent to form a solvent-aqueous alumina mixture, c. drying said solvent-aqueous alumina mixture to produce alumina, and d. forming said alumina into particles and calcining to produce said gamma alumina.

13. The process of claim 12 wherein said particles of (d) have a loose bulk density from about 15 to about 35 lb/ft$^3$, a cumulative pore volume from about 0.8 to about 2.0 cc/g, and a surface area from about 150 to about 350 m$^2$/g.

* * * * *

UNITED STATES PATENT OFFICE
CERTIFICATE OF CORRECTION

PATENT NO. : 4,051,017
DATED : September 27, 1977
INVENTOR(S) : William R. Beaty, Jr.

It is certified that error appears in the above-identified patent and that said Letters Patent are hereby corrected as shown below:

Column 1, line 34, after are, "of" left out.

Column 1, line 38, "d" left off improve.

Column 3, line 5, "to" second occurrence, should be --of--.

Column 4, line 19, "is" should be --in--.

Column 5, line 1, "in" should be --is--.

Column 5, line 24, "oxalazes" should be --oxalates--.

Signed and Sealed this

Twenty-first Day of March 1978

[SEAL]

Attest:

RUTH C. MASON
Attesting Officer

LUTRELLE F. PARKER
Acting Commissioner of Patents and Trademarks